(12) United States Patent
Pion (10) Patent No.: US 9,746,438 B2
(45) Date of Patent: Aug. 29, 2017

(54) HUMIDITY SENSOR WITH TEMPERATURE COMPENSATION

(71) Applicant: Veris Industries, Inc., Tualatin, OR (US)

(72) Inventor: Albert Pion, Tigard, OR (US)

(73) Assignee: Veris Industries, LLC, Tualatin, OR (US)

( * ) Notice: Subject to any disclaimer, the term of this patent is extended or adjusted under 35 U.S.C. 154(b) by 244 days.

(21) Appl. No.: 14/156,252

(22) Filed: Jan. 15, 2014

(65) Prior Publication Data

US 2014/0216153 A1    Aug. 7, 2014

Related U.S. Application Data

(60) Provisional application No. 61/761,380, filed on Feb. 6, 2013.

(51) Int. Cl.
| | | |
|---|---|---|
| *G01N 27/12* | (2006.01) | |
| *G01N 27/22* | (2006.01) | |
| *G01N 27/04* | (2006.01) | |

(52) U.S. Cl.
CPC ......... *G01N 27/225* (2013.01); *G01N 27/048* (2013.01); *G01N 27/123* (2013.01)

(58) Field of Classification Search
CPC . G01N 27/048; G01N 27/225; H04J 11/0023; H04W 72/02
USPC .... 73/23.2, 29.01, 29.02, 74, 335.02–335.05
See application file for complete search history.

(56) References Cited

U.S. PATENT DOCUMENTS

| | | | |
|---|---|---|---|
| 4,368,639 A | 1/1983 | Owens | |
| 4,379,406 A * | 4/1983 | Bennewitz | G01N 27/121 |
| | | | 324/696 |
| 5,652,382 A * | 7/1997 | Nakagawa | G01N 27/048 |
| | | | 324/678 |
| 5,844,138 A | 12/1998 | Cota | |
| 6,122,972 A | 9/2000 | Crider | |
| 6,170,345 B1 | 1/2001 | Kerner | |
| 6,241,950 B1 | 6/2001 | Veelenturf et al. | |
| 6,777,120 B2 * | 8/2004 | Nelson | G01N 25/56 |
| | | | 429/413 |
| 6,852,216 B2 | 2/2005 | Moscaritolo et al. | |
| 6,895,803 B2 * | 5/2005 | Seakins | G01N 27/223 |
| | | | 73/23.2 |
| 6,941,193 B2 | 9/2005 | Frecska et al. | |
| 7,049,829 B2 * | 5/2006 | Luthi | G01N 27/225 |
| | | | 324/664 |
| 7,267,002 B2 * | 9/2007 | Itakura | G01D 5/24 |
| | | | 324/670 |
| 7,421,911 B2 | 9/2008 | Desrochers et al. | |
| 7,498,823 B2 * | 3/2009 | Cerutti | G01N 27/121 |
| | | | 219/497 |
| 7,661,327 B2 | 2/2010 | Bourgein et al. | |
| 2002/0078733 A1 * | 6/2002 | Seakins | G01N 27/223 |
| | | | 73/29.02 |
| 2004/0182132 A1 | 9/2004 | Head | |
| 2005/0028588 A1 * | 2/2005 | Mitter | G01N 27/223 |
| | | | 73/335.04 |
| 2005/0066711 A1 | 3/2005 | Discenzo | |

(Continued)

*Primary Examiner* — Randy Gibson
*Assistant Examiner* — Gedeon M Kidanu
(74) *Attorney, Agent, or Firm* — Chernoff Vilhauer McClung & Stenzel, LLP (57) ABSTRACT

A gas sensing device that includes humidity compensation.

8 Claims, 7 Drawing Sheets

(56) References Cited

U.S. PATENT DOCUMENTS

| | | | |
|---|---|---|---|
| 2006/0037393 A1* | 2/2006 | Itakura | G01D 5/24 |
| | | | 73/335.04 |
| 2006/0107774 A1 | 5/2006 | Meyberg | |
| 2007/0137318 A1 | 6/2007 | Desrochers et al. | |
| 2007/0295084 A1* | 12/2007 | Chang | G01N 27/048 |
| | | | 73/335.02 |
| 2008/0178694 A1 | 7/2008 | Barford et al. | |
| 2008/0257037 A1* | 10/2008 | Isogai | G01N 27/225 |
| | | | 73/335.04 |
| 2009/0114536 A1* | 5/2009 | Ishiguro | G01N 33/0016 |
| | | | 204/406 |
| 2009/0122834 A1* | 5/2009 | Wang | G01K 7/21 |
| | | | 374/185 |
| 2011/0138908 A1* | 6/2011 | Liu | G01N 27/223 |
| | | | 73/335.04 |
| 2013/0133420 A1* | 5/2013 | Huang | G01N 27/121 |
| | | | 73/335.05 |
| 2013/0139587 A1* | 6/2013 | Le Neel | G01N 27/223 |
| | | | 73/335.04 |

\* cited by examiner

HUMIDITY SENSOR WITH TEMPERATURE COMPENSATION

CROSS-REFERENCE TO RELATED APPLICATIONS

This application claims the benefit of U.S. Provisional App. No. 61/761,380, filed Feb. 6, 2013.

BACKGROUND OF THE INVENTION

The present invention relates generally to a humidity sensor with temperature compensation.

A humidity sensor is a device used for measuring the moisture content in an environment. Humidity sensors typically rely on the measurement of some other property than humidity such as a change in mass, a change in electrical capacitance, and/or a change in electrical resistance of a substance as moisture is absorbed or discharged. In particular, with respect to capacitive based humidity sensors, the humidity has an effect on a dielectric constant of a polymer substance, metal oxide substance, or otherwise. The change in the dielectric constant is measured to determine the humidity. In particular, with respect to resistive based humidity sensors, the humidity has an effect on the electrical resistance of a conductive polymer, conductive salt, or otherwise. The change in the electrical resistance is measured to determine the humidity. Unfortunately, the accuracy of humidity sensors is limited due to many factors, including for example, temperature, contamination, drift, hysteresis, and/or aging effects.

What is desired therefore is a humidity sensor with temperature compensation to improve its accuracy.

The foregoing and other objectives, features, and advantages of the invention may be more readily understood upon consideration of the following detailed description of the invention, taken in conjunction with the accompanying drawings.

DETAILED DESCRIPTION OF PREFERRED EMBODIMENT

Figure 1:
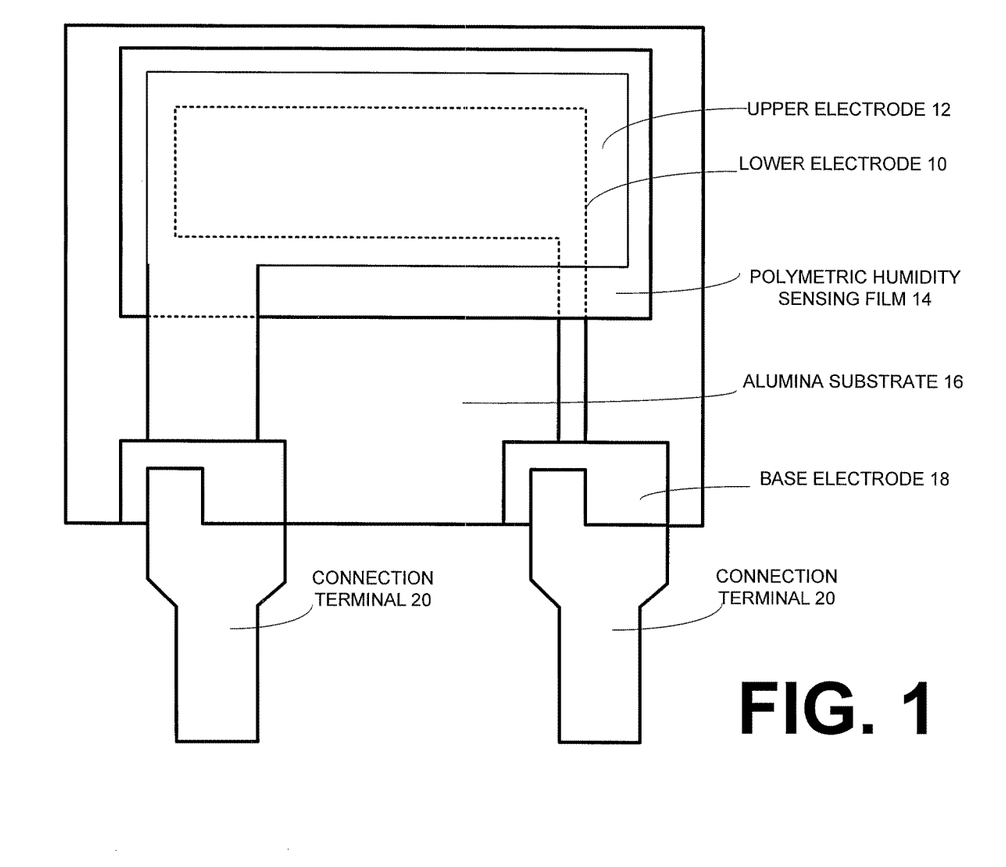
FIG. 1 illustrates a cut away of a capacitive sensor.

Referring to FIG. 1, an exemplary capacitive humidity sensor is illustrated. Humidity sensors relying on this principle may consist of a hygroscopic dielectric material sandwiched between a pair of electrodes, namely a lower electrode 10 and an upper electrode 12, forming a small capacitor. Most capacitive sensors use a plastic or polymer as the dielectric material 14, with a typical dielectric constant ranging from 2 to 15. The capacitive sensor may include an alumina substrate 16, a base electrode 18, and connection terminals 20. In absence of moisture, the dielectric constant of the hygroscopic dielectric material 14 and the sensor geometry determine the value of capacitance. At typical room temperature, the dielectric constant of water vapor may have a value of about 80, a value which is substantially larger than the constant of the sensor dielectric material. Therefore, subsequent absorption of water vapor by the sensor results in an increase in sensor capacitance. At equilibrium conditions, the amount of moisture present in a hygroscopic material 14 primarily depends on both the ambient temperature and the ambient water vapor pressure. At equilibrium conditions, of the amount of moisture present in a hygroscopic material primarily depends on both the ambient temperature and the ambient water vapor pressure are likewise applicable to any hygroscopic dielectric material used on the sensor.

Relative humidity is a function of both the ambient temperature and water vapor pressure. Therefore there is a relationship between relative humidity, the amount of moisture present in the sensor, and sensor capacitance. This relationship primarily governs the operation of the capacitive humidity sensor.

On an alumina substrate 16, the lower electrode 10 is often formed using gold, platinum and/or other material. The polymer layer 14 such as PVA is deposited on the lower electrode 10. This polymer layer 14 senses the ambient humidity. On top of this polymer layer 14, a gold upper layer 12 (or other material) is deposited which acts as a top electrode. The upper electrode 12 also allows water vapor to pass through it, into the sensing polymer layer 14. The water vapors enter and/or leave the hygroscopic sensing layer until the vapor content is in equilibrium with the ambient air or gas. Accordingly, preferably the capacitive humidity sensor is principally a capacitive element that includes a humidity sensitive material therein. As the relative humidity increases the capacitance increases. As the relative humidity decreases the capacitance decreases. The relative percentage of the actual vapor pressure (P) compared to the saturated vapor pressure ($P_s$) may be characterized as follows: RH= $(P/P_S)*100\%$. Other types of capacitive humidity sensors may likewise be used, such as for example, multi-walled carbon nanotubes.

Figure 2:
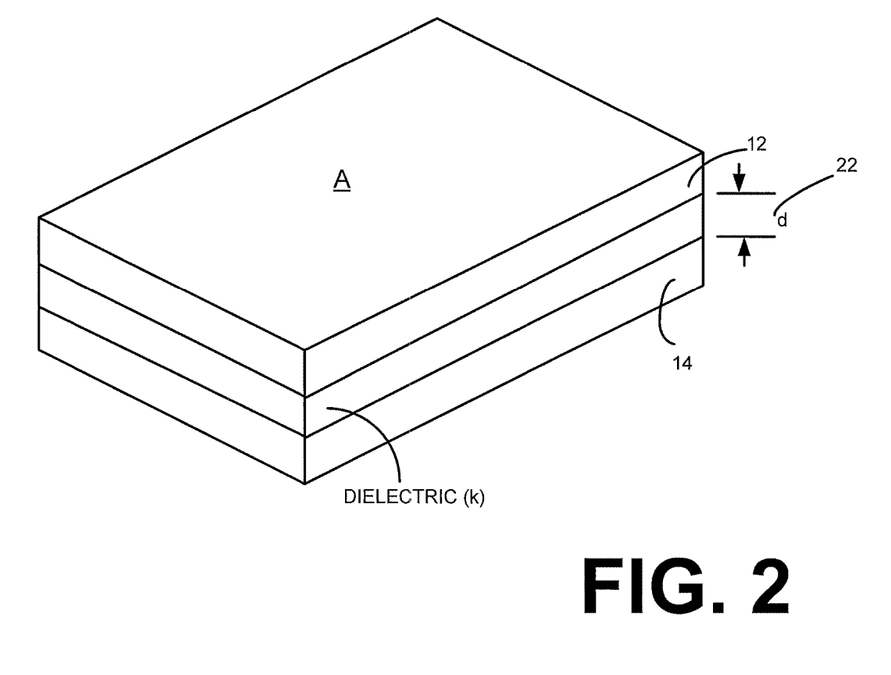
FIG. 2 illustrates layers of a capacitive sensor.
Figure 3:
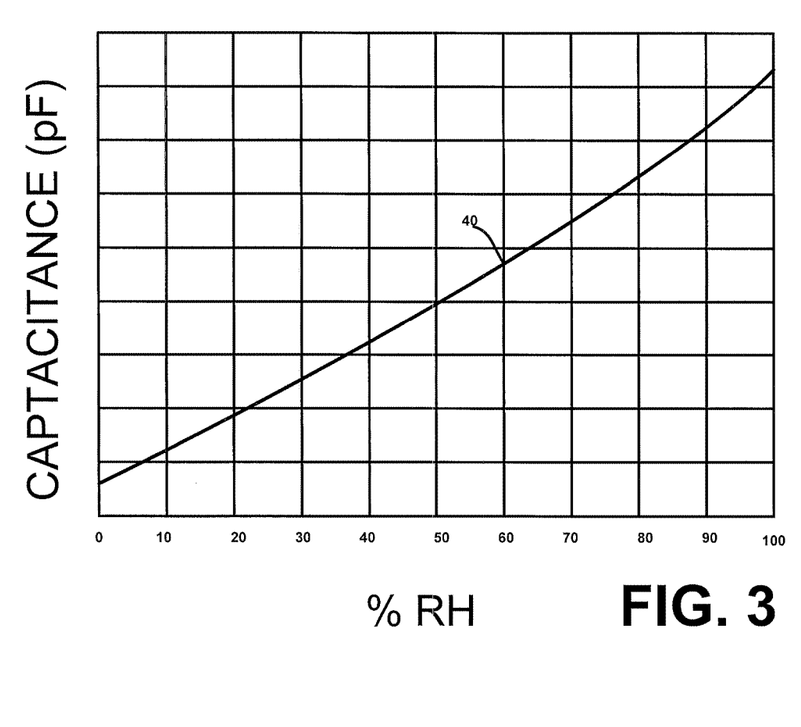
FIG. 3 illustrates a capacitance versus relative humidity graph.

Referring to FIG. 2, the capacitance is dependent on the constant (k) of the dielectric, which is in turn dependent on the relative humidity and temperature (T) of the dielectric. This relationship may be characterized as $C=k_o*\in_o*A/d$, where d is the distance 22 between the conductive layers 12, 14, and A is the area of the conductive plates. For moist air the dielectric may be calculated by the following relationship, $k=1+(211/T)*(P+(48P_S/T)*RH)*10^{-6}$, where k typically has a linear relationship to the relative humidity (RH) and the capacitance has a non-linear relationship to the relative humidity. Referring to FIG. 3, this non-linear relationship 40 is characterized for the sensor so that the device may be calibrated.

Figure 4:
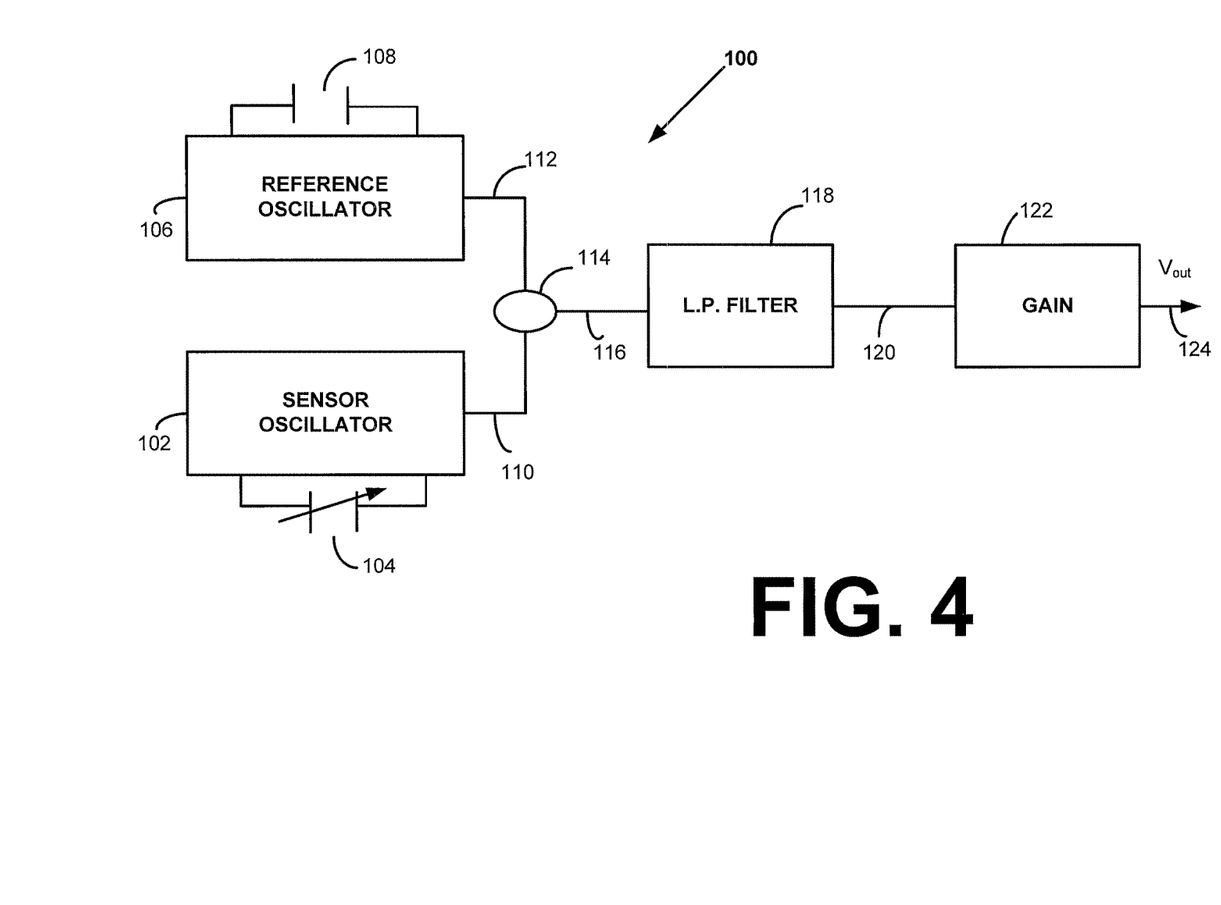
FIG. 4 illustrates a capacitance detector circuit.

Referring to FIG. 4, one exemplary technique to sense the changing capacitance of the sensor is to use a signal conditioning circuit 100. A sensor oscillator 102 changes it oscillation frequency based upon a change in the capacitance 104 of a sensor. A reference oscillator 106 has a fixed oscillation frequency that is based upon the reference capacitor 108. The output 110 of the sensor oscillator 102 and the output 112 of the reference oscillator are combined 114 with one another to provide a signal 116 that is related to a change in the sensor oscillator capacitance 104. A low pass filter 118 attenuates the oscillation frequencies leaving a voltage response 120 that is related to the change in the sensor oscillator capacitance 104. An amplifier 122 amplifies the voltage response 120 to a desired output voltage range 124. Other capacitive sensor sensing techniques may likewise be used.

Figure 5:
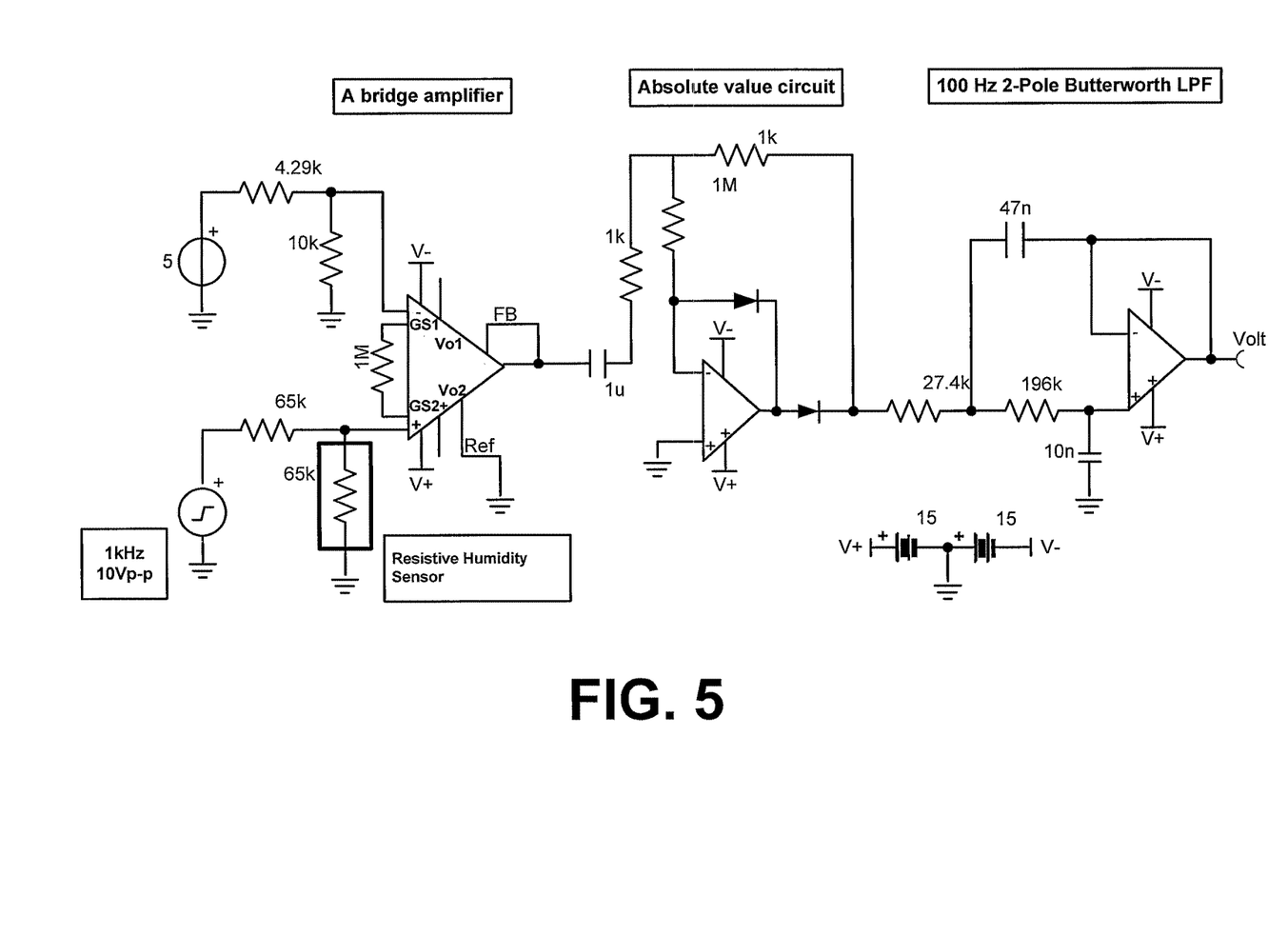
FIG. 5 illustrates a resistive detector circuit.

For resistive based humidity sensors many different signal conditions circuits may be used. Referring to FIG. 5 for example, a 1 kHz alternating current sine wave may be used to excite a half-bridge circuit which includes the resistive humidity sensor. The output voltage of the half-bridge circuit is proportional to the voltage divider voltage established by the upper resistor and resistive sensor. Exciting the resistive humidity sensor with the alternating current signal reduces the sensor polarization that would occur as a result of a direct current voltage. A direct current pedestal voltage is applied to an inverting input by way of a voltage divider. This direct current voltage is subtracted from the alternating current voltage by an amplifier resulting in a difference voltage output. The direct current level results in the difference voltage at the two inputs results in an increasing output voltage as the voltage difference increases. The output of the AC bridge amplifier is then AC coupled, to remove the DC content, to the absolute value circuit which performs a full-wave rectifier function. The rectified voltage is then applied to the input of a two-pole low-pass filter. This removes most of the 1-kHz ripple.

Unfortunately, the process by which the gaseous molecules enter and leave the sensor material is non-linear and complicated. For example, typically the sensor is calibrated to an operating temperature range before being used. Often the calibration is inaccurate due to in-batch variations, batch-to-batch variations, temperature changes, limited precision of a calibration reference, and the lack of stability of the sensors over time. In addition to such calibration inaccuracies, a hysteresis exists in the sensor material at different points accruing from a dry environment on the one hand and a humid environment on the other hand, provided enough dwell time exists at each point.

Figure 6:
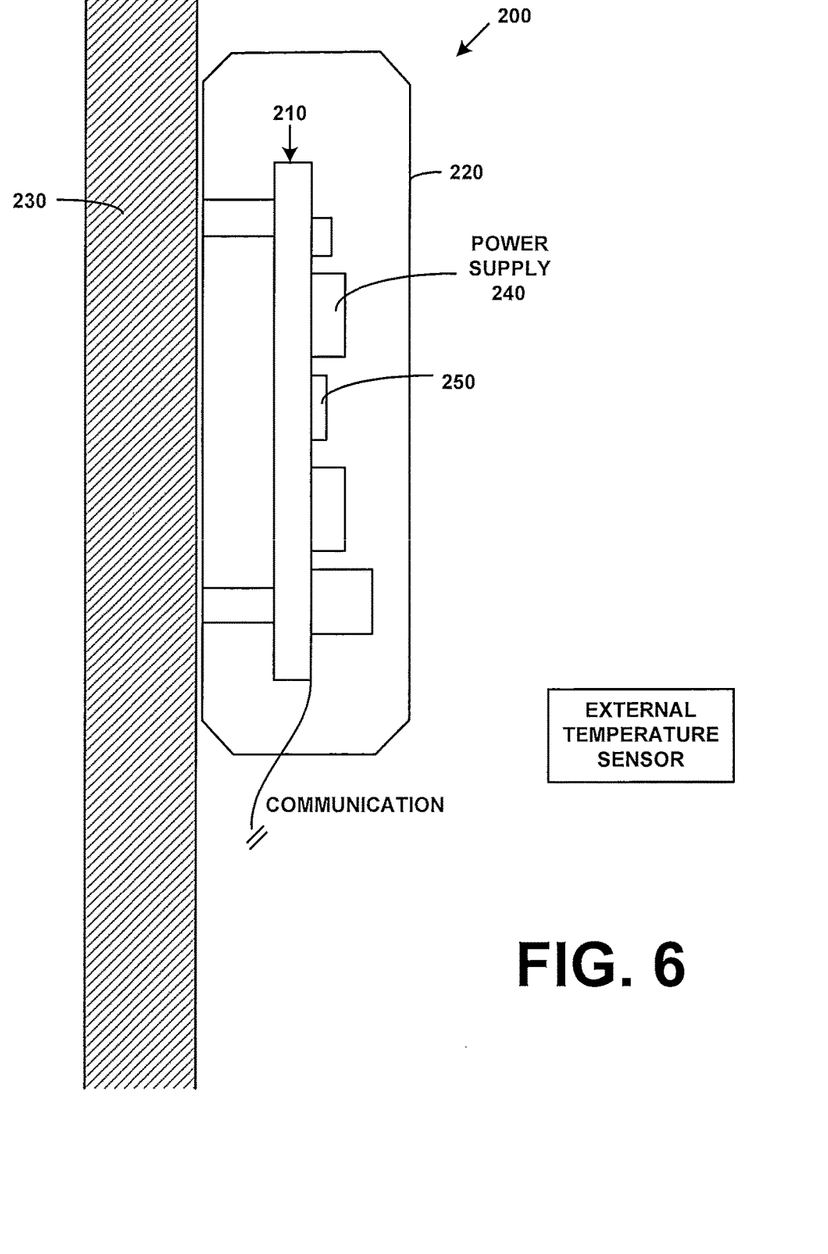
FIG. 6 illustrates a humidity sensor with temperature compensation.

Referring to FIG. 6, a humidity sensor 200 tends to have a significant number of electronic components 210 therein, such as a microprocessor, a memory circuit, multiple resistors, multiple capacitors, multiple inductors, humidity sensing elements with electronics, power conditioning elements, electronic safety elements, display devices, communication electronics, etc., supported by a circuit board The humidity sensor 200 often includes a substantially enclosed housing 220 that contains the electronic components 210 therein together with vents to dissipate some heat generated by the electronic components 210. Often, the humidity sensor 200 is attached to a vertical wall 230 of a structure. The heat that is generated by the electronic components 210 within the housing 220 tends to vary over time as a result of environmental and/or operational conditions. For example, if the humidity sensor 200 is installed in a cold environment with a lot of ventilation resulting in substantial air movement, then the electronic components 210 do not tend to heat up the humidity sensor substantially. For example, if the humidity sensor is installed in a moderate environment without any ventilation resulting in no substantial air movement, then the electronic components 210 tend to substantially heat up the humidity sensor 200. For example, if the humidity sensor is configured to provide continual measurement and transmission of measured data, the electronic components 210 will tend to create more heat than if the humidity sensor is configured to provide intermittent measurement and transmission of measured data. For example, if the humidity sensor is configured to transmit generally raw measured data, the electronic components 210 will tend to create less heat then if the humidity sensor is configured to process the data and transmit the processed data. For example, some of the electronic components 210 of the humidity sensor may tend to age over time or otherwise not be as tuned with one another as desired, thus tending to generate additional heat than would otherwise be the case.

The heat being dissipated by the electronic components 210 within the humidity sensor housing 220 alters the humidity measurements of the humidity sensor, since the resulting gas pressure within the humidity sensor housing 220 is modified with respect to the exterior of the sensor housing. Moreover, with the variations in the operation of the electronic components together with variations in the operating environment, a suitable modification of the sensed humidity within the humidity housing at any particular time, to account for the current heat generation, will likewise vary.

To account for the change in the temperature within the humidity sensor housing, as a result of the electronic components, it is desirable to characterize the heat resulting from the operation of the electronic components. The heat resulting from the operation of the electronic components may be characterized by the power provided to the humidity sensor 200 from a power supply 240. A temperature sensor 250 may be included within the housing, either as part of the electronic components 210 or otherwise included for characterization purposes, that senses the internal temperature of the humidity housing 220. The electronic components 210 may include a voltage measurement process to sense the supply voltage to the humidity sensor 200. Often the voltage measurement process includes an analog to digital converter to provide a signal to the microcontroller representative of the voltage level. The electronic components 210 may include a current measurement process to sense the supply current to the humidity sensor 200. Often a current sensing process includes a current transformer or a resistive shunt together with an analog to digital converter to provide a signal to the microcontroller representative of the current level. A power factor may likewise be determined, if desired. By multiplying the voltage level by the current level, together with the power factor if appropriate, may be used to determine the instantaneous power and/or average power (generally referred to as power) being consumed by the humidity sensor 200.

It is desirable to characterize the humidity housing 220 to determine its thermal resistance in degrees C. per watt (Rt) dissipated by an internal heat source, such as the electronic components 210. The difference in temperature may be the difference between the ambient temperature (such as measured by an external temperature sensor) and the internal temperature (such as measured by an internal temperature sensor 250) divided by the power used (such as measured at the input to the humidity sensor such as from a power supply). Often the voltage is maintained relatively constant from a power source so the humidity sensor may include a current adjustment to change the amount of current down from the power source so that the resulting different temperatures as a result of heating may be characterized. Thus the increase in the temperature as a result of operation of the humidity sensor under typical operating conditions and a typical operating environment may be characterized relative to the watts being consumed by the humidity sensor. The thermal resistance may be characterized at different ambient temperatures, if desired. The thermal resistance may be characterized as a result of different power used, if desired. The thermal resistance may be characterized as a result of different operating conditions, if desired. The thermal resistance may be characterized as a result of different operating environments, if desired. The thermal resistance may be characterized as a result of aging, if desired. The characterization of the thermal resistance may likewise be linear or non-linear, as desired.

Figure 7:
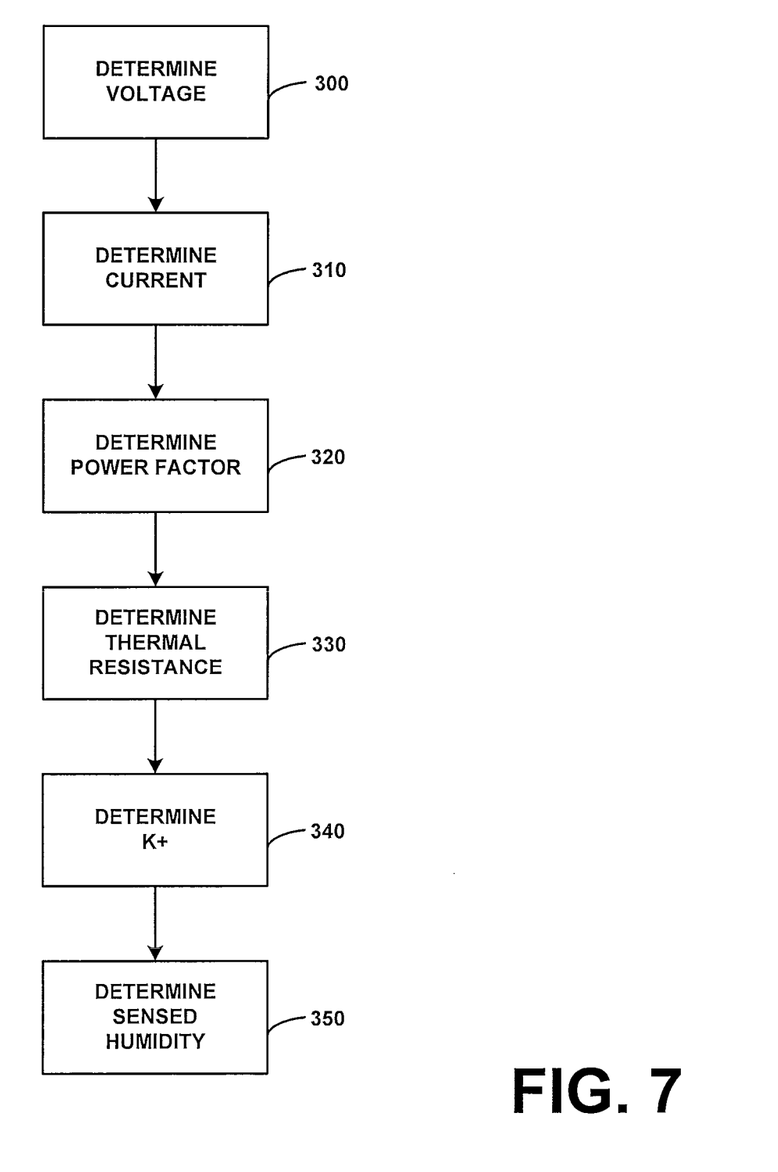
FIG. 7 illustrates a humidity sensor temperature compensation technique.

Referring to FIG. 7, during the operation of the humidity sensor the microcontroller may read the voltage (V) 300 and the current (I) 310, together with the power factor 320, if desired, to determine the power being dissipated by the electronic components of the humidity sensor. The voltage may be set to a predetermined value, if desired. The power factor may be set to unity, if desired. The power is then multiplied by the humidity sensor's thermal resistance 330 to estimate the differential temperature as a result of self-heating Kt 340. The thermal resistance may be further characterized based upon one or more of the aforementioned factors. This may be characterized as, Kt=Power*Rt=Voltage*Current*Rt.

The microcontroller may subtract kt from the internal temperature sensed by an internal temperature sensor 250 of the humidity sensor 200. The result of the subtraction provides an estimation of the temperature outside of the humidity housing. The estimation of the external temperature to the humidity housing may be used as the basis to modify 350 the output of the humidity sensor so that an adjusted humidity value is provided that accounts for the temperature differential. Preferably, the humidity sensor does not include an external temperature sensor or otherwise does not use the external humidity sensor for adjustment related to internal heating as a result of power dissipation.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:
1. A humidity sensor comprising:
 (a) a humidity sensitive element within a housing that senses the humidity and provides a humidity estimate of said humidity to a microprocessor;
 (b) a sensing circuit that senses power provided to electronic components of said humidity sensor, including a microprocessor of said sensing circuit, from a power source;
 (c) an internal temperature sensor enclosed within said housing and provides an internal temperature signal to said microprocessor;
 (d) said microprocessor modifying said humidity estimate based upon (1) said internal temperature signal, (2) a thermal resistance of said humidity sensor, and (3) said power including said power to said microprocessor.

2. The humidity sensor of claim 1 wherein said humidity sensitive element said provides said humidity estimate of said humidity based upon a capacitive measurement.

3. The humidity sensor of claim 1 wherein said humidity sensitive element said provides said humidity estimate of said humidity based upon a resistive measurement.

4. The humidity sensor of claim 1 wherein said housing enclosing said internal temperature sensor also encloses said sensing circuit, and said microprocessor.

5. The humidity sensor of claim 1 wherein said microprocessor is free from modifying said humidity estimate based upon a temperature sensor that senses ambient air temperature external to said housing enclosing said humidity sensitive element.

6. The humidity sensor of claim 1 wherein said thermal resistance is a constant.

7. The humidity sensor of claim 1 wherein said microprocessor said modifies said humidity estimate based upon a voltage provided to said electronic components.

8. The humidity sensor of claim 7 wherein said microprocessor said modifies said humidity estimate based upon a power provided to said electronic components.

* * * * *

UNITED STATES PATENT AND TRADEMARK OFFICE
CERTIFICATE OF CORRECTION

PATENT NO. : 9,746,438 B2
APPLICATION NO. : 14/156252
DATED : August 29, 2017
INVENTOR(S) : Albert Pion Page 1 of 1

It is certified that error appears in the above-identified patent and that said Letters Patent is hereby corrected as shown below:

In the Specification

Column 2, Line 57:
Change "it" to read –its–.

Column 3, Line 5:
Change "conditions" to read –condition–;

Column 3, Line 44:
After "circuit board" insert a --.--.

Signed and Sealed this
Twenty-sixth Day of June, 2018

Andrei Iancu
*Director of the United States Patent and Trademark Office*